United States Patent
Dunbar et al.

[11] Patent Number: 6,162,456
[45] Date of Patent: Dec. 19, 2000

[54] ADHESIVE TRANSDERMAL DRUG DELIVERY MATRIX OF A PHYSICAL BLEND OF HYDROPHILIC AND HYDROPHOBIC POLYMERS

[75] Inventors: Darth Dunbar, Redwood City; Kuldeepak Sharma, Fremont, both of Calif.

[73] Assignee: Ortho-McNeil Pharmaceutical, Inc., Raritan, N.J.

[21] Appl. No.: 07/950,606

[22] Filed: Sep. 24, 1992

[51] Int. Cl.$^7$ .............. A61F 13/02; B32B 15/04; C08L 15/00
[52] U.S. Cl. .............. 424/448; 424/449; 424/487; 428/343; 428/349; 523/111
[58] Field of Search .............. 424/448, 449, 424/487; 523/111; 428/343, 349

[56] References Cited

U.S. PATENT DOCUMENTS

| | | | |
|---|---|---|---|
| 3,969,308 | 7/1976 | Penneck . | |
| 4,112,213 | 9/1978 | Waldman | 523/111 |
| 4,668,506 | 5/1987 | Bawa | 424/429 |
| 4,710,536 | 12/1987 | Klingen | 428/343 |
| 4,713,244 | 12/1987 | Bawa et al. | 424/429 |
| 4,737,410 | 4/1988 | Kantner | 428/343 |
| 4,857,313 | 8/1989 | Song et al. | 424/81 |
| 4,871,812 | 10/1989 | Lucast et al. | 525/186 |
| 4,898,920 | 2/1990 | Lee et al. | 525/477 |
| 4,904,247 | 2/1990 | Therriault et al. | 604/304 |
| 4,906,463 | 3/1990 | Cleary | 514/785 |
| 5,035,894 | 7/1991 | Lee et al. | 424/448 |
| 5,133,970 | 7/1992 | Petereit | 424/448 |
| 5,176,916 | 1/1993 | Yamanaka | 424/449 |
| 5,474,783 | 12/1995 | Miranda et al. | 424/448 |

FOREIGN PATENT DOCUMENTS 0326278  8/1989  European Pat. Off. .

OTHER PUBLICATIONS

Ulman et al., *Jornal of Controlled Release* (1989) 10:251–260.

Primary Examiner—Thurman K. Page
Assistant Examiner—Isis Ghali

[57] ABSTRACT

Adhesive matrixes for use in administering drugs transdermally in which the adhesive component is a homogenous physical blend of a hydrophilic polymer adhesive and a hydrophobic polymer adhesive. The blends provide enhanced drug flux as compared to adhesive matrixes of either the hydrophobic polymer adhesive or hydrophilic polymer adhesive alone.

17 Claims, 3 Drawing Sheets

ADHESIVE TRANSDERMAL DRUG DELIVERY MATRIX OF A PHYSICAL BLEND OF HYDROPHILIC AND HYDROPHOBIC POLYMERS

DESCRIPTION

1. Technical Fields

This invention is in the fields of pressure sensitive adhesive compositions and transdermal drug delivery. More particularly, it concerns an adhesive transdermal drug delivery matrix composed of a physical blend of hydrophilic and hydrophobic polymers.

2. Background Art

One of the simplest transdermal drug delivery device structures is a bilaminate of a backing layer and an underlying matrix layer composed of a pressure sensitive adhesive loaded with a drug. In use the basal surface of the matrix is applied directly to the patient's skin and the drug migrates by diffusion from the matrix into the adjoining skin. Prior to use the basal surface of the matrix is covered with a removable release liner layer.

Both hydrophilic and hydrophobic pressure sensitive adhesives have been used in transdermal drug delivery matrixes.

Silicones, polyisobutylene (PIB), and solvent-based acrylates are the more commonly used hydrophobic type of adhesive. Correspondingly, water-based acrylates are frequently suggested as hydrophilic matrixes for transdermal drug delivery.

The principal criteria of pressure sensitive adhesives for use in such transdermal drug delivery devices are that they: be compatible with components of the drug formulation (e.g., the drug itself, and any excipient, penetration enhancer, stabilizer or other additive); not irritate or otherwise deleteriously affect the skin; provide the requisite skin adhesion over the wearing time of the device; and provide the desired release rate profile for the desired drug. This latter criterion—release rate profile—is primarily a function of the solubility of the drug in the adhesive, the diffusion coefficient of the adhesive, and the concentration of drug in the adhesive matrix. In view of these parameters, hydrophobic adhesives are typically used with hydrophobic drugs and correspondingly, hydrophilic adhesives are used with hydrophilic drugs.

Hydrophilic adhesives typically exhibit a longer lag time (the time it takes for flux to rise to significant levels) and a higher ultimate flux than hydrophobic adhesives. In contrast, the hydrophobic adhesives typically exhibit shorter lag times when used with hydrophobic drugs (they exhibit low release rates with hydrophilic drugs) and better adhesiveness than hydrophilic adhesives over long wearing times. One object of the present invention is provide an adhesive matrix that has the advantageous properties of both the hydrophobic and hydrophilic matrixes.

Prior patents have suggested using blends of polymers as adhesives in transdermal matrixes or in other medical settings.

U.S. Pat. Nos. 4,898,920 and 5,035,894 (see also J. Cont. Rel. (1989) 10:251–260 and 273–281) describe the use of blends of polyethylene oxide (PEO) grafted siloxane copolymers and resinous siloxane copolymers as adhesives in transdermal drug delivery. The presence of the grafted PEO increases the hydrophilicity of the siloxane copolymer but the grafting is below the level which makes the copolymer water soluble (i.e., Z in the chemical formula for the copolymer is $\leq 15$—col. 4, line 63 and col. 6, line 9). The patent indicates that the grafting of PEO onto the siloxane copolymer enhanced the release rate of hydrophilic drugs but did not affect the release rate of hydrophobic drugs (see Example 5 of '920). In contrast to this patent the hydrophilic component of the invention matrix is water soluble and the presence of the hydrophilic component enhances the release rate of both hydrophobic as well as hydrophilic drugs.

U.S. Pat. No. 4,737,410 describes blends of acrylate/methacrylate copolymers and polyalkyloxazolines. The patent says these polymers are blended in solution and are miscible in the sense that no discrete particles greater than 4000 Å of either component are present in the blend. Further, there is no suggestion to use these blends as transdermal drug delivery matrixes.

U.S. Pat. No. 4,871,812 describes blends of an acrylate terpolymer which has a hydrophilic component and a carboxyamido group containing polymer. The terpolymers themselves are not water-soluble and the blends are said to be nonswellable. There is no suggestion to use these blends as transdermal drug delivery matrixes.

DISCLOSURE OF THE INVENTION

One aspect of the present invention is an adhesive transdermal drug delivery matrix comprising a homogeneous physical blend of:

(a) a drug that is capable of transdermal administration;

(b) a water-soluble hydrophilic polymer that is permeable to the drug; and (c) a hydrophobic adhesive polymer that is permeable to the drug and substantially immiscible with the hydrophilic polymer, wherein the hydrophilic polymer constitutes about 1% to 90% by weight of the total of the hydrophilic and hydrophobic polymers, the hydrophobic polymer constitutes about 10% to 99% by weight of the total of the hydrophilic and hydrophobic polymers and the flux of drug the blend is significantly greater than the flux of drug from either (b) or (c) alone.

Another aspect of the present invention is a transdermal drug delivery device comprising a laminated composite of:

(a) a backing layer; and (b) the above-described matrix.

MODES FOR CARRYING OUT THE INVENTION

Figure 1:
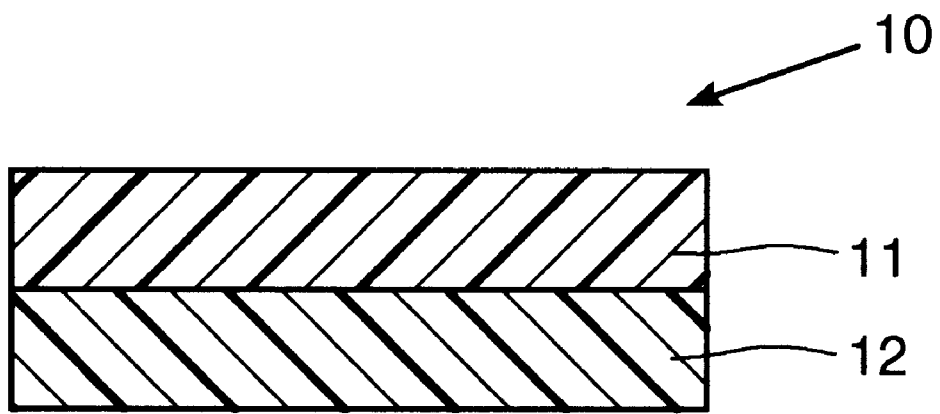
FIG. 1 is a schematic diagram of an embodiment of a transdermal drug delivery device which has a matrix according to this invention.

As used herein the term "drug" intends a biologically active compound or mixture of compounds that has a therapeutic, prophylactic or other beneficial effect on the individual to whom the compound or compounds is administered. Drugs that are capable of transdermal administration via the mechanism of passive diffusion are those drugs that have physico-chemical properties (e.g., molecular weight) that permit them to permeate through a reasonably sized (i.e., 200 $cm^2$ or less, preferably 20 $cm^2$ to 100 $cm^2$) area of skin with or without the assistance of skin permeation enhancers at rates that achieve the desired therapeutic, prophylactic, or beneficial effect. The drug may be hydrophilic or hydrophobic. Examples, without limitation, of hydrophobic drugs are xanax, tamoxifen, buprenorphine, progesterone, and estradiol. Hydrophilic drug examples are nicardipine hydrochloride, methylsalicylic acid, and nitroglycerine. As used herein the term "physical blend" denotes a mixture of the hydrophilic and hydrophobic polymers of the invention in which there are no chemical bonds between the two polymers.

As used herein the term "homogenous" denotes a physical blend of the hydrophilic and hydrophobic polymers in which there is substantially no discernible phase separation therebetween when viewed without magnification by a normal human eye at room temperature.

As used herein the term "substantially immiscible" intends that the hydrophilic polymers and hydrophobic polymers are not soluble in each other (i.e. solubility is less than 5 parts in 95 parts at 25° C.) and are present in the blend as discrete particles at a microscopic level.

As used herein with respect to polymer components of the matrix, the term "water soluble hydrophilic" intends a polymer that is greater than 20% by weight soluble in water at 32 °C. over 24 hrs.

As used herein with respect to polymer components of the matrix the term "hydrophobic" intends a polymer that is less than 20% by weight soluble on water at 32° C. over 24 hrs.

As used herein with respect to drugs, the term "hydrophilic" intends a drug that has a solubility of at least one mg/L in water at 32° C.

As used herein with respect to drugs, the term "hydrophobic" intends a drug that has a solubility of less than one mg/L in water at 32° C.

As used herein the term "flux" intends the rate transfer of drug from the matrix as measured by the in vitro test described in Proceeding of the 19th Symposium of Controlled Release Society, 1992, Page 464 and U.S. Pat. No. 5,069,909.

The hydrophilic and hydrophobic adhesives that form the invention matrix are polymers or mixtures of polymers that exhibit pressure sensitive adhesion to human skin. Pressure sensitive adhesion is a well-documented phenomenon (see Honerink and Salomn "*Adhesion and Adhesives*" Vol. 2, Ch. 17 Elisvier Publishing Company (1967) and *Handbook of Pressure Sensitive Adhesive Technology,* 2nd Ed., Van Nostrand Reinhold Company (1989). These adhesives are medically acceptable in the sense that they do not unduly irritate, sensitize or otherwise damage or deleteriously affect living human skin. These polymers are also permeable to the drug being administered in that the drug is capable of diffusing through the polymers. In this regard the diffusion coefficient of the drug in the polymers will normally be $1\times10^{-7}$ to $1\times10^{-8}$ cm/sec. In addition the polymers should be compatible with the drug in the sense that they should not react with, degrade, deactivate or otherwise affect the drug adversely. Examples of hydrophobic polymer adhesives that may be used in the matrix are polysiloxanes (silicones), polyisobutylene, polyethylene, polystyrene-butadiene copolymers, polyurethanes, and polyether block amide copolymers. Preferred hydrophobic polymer adhesives are polysiloxanes. Examples of hydrophilic polymer adhesives that may be used in the matrix are methacrylic acid copolymers, acrylate copolymers, cellulose derivatives, polyvinyl alcohols, and polyacrylamides. Preferred hydrophilic polymer adhesives are methacrylic acid copolymers such as those sold under the GELVA and PLASTOID trademarks.

The relative proportions of the hydrophobic and hydrophilic polymer adhesives in the matrix will depend upon the particular drug to be incorporated in the matrix, the particular polymers selected and the desired flux to be achieved. In general matrixes for delivering hydrophobic drugs will typically contain a relatively higher proportion of hydrophilic polymer. Correspondingly, matrixes for delivering hydrophilic drugs may contain higher proportions of hydrophobic polymer. Normally the hydrophilic polymer will constitute about 1% to 90% by weight of the total polymer content, more usually 50% to 90% by weight of the total polymer content. When a hydrophobic drug is being delivered, the proportion of hydrophilic polymer in the matrix is typically greater than 50% by weight. Correspondingly, the hydrophobic polymer will normally constitute about 10% to 99% by weight of the total polymer content, more usually 25% to 50% by weight of the total polymer content. As indicated, when a hydrophobic drug is involved the proportion of hydrophobic polymer is normally less than 50%.

The loading of drug in the matrix may also vary depending upon the particular drug and matrix involved, the intended therapy, and the desired duration of administration. Normally, the matrix will contain sufficient drug to provide effective amounts thereof to the wearer over a period of 0.5 to 14 days, more usually 1 to 7 days. In this regard the drug will normally be present at or above its saturation concentration in the matrix and constitute 3% to 30% by weight of the matrix, more usually 1% to 15% by weight of the matrix.

The flux of drug from the matrix of the invention is significantly greater than the flux of drug from a matrix composed of only one of the polymers and the drug. In most instances the flux of drug from the matrix of the invention will be at least 30% greater (measured as an average over the time period over which the matrix is to be worn on the skin) than the flux of drug from a matrix composed of only one of the polymers and the drug. Preferably, the flux will be 3 to 4 times greater.

The matrix may contain other components used in transdermal matrixes, such as skin permeation enhancers, anti-irritants, solubilizers, and emulsifiers. These components will typically be present, if at all, in minor proportions in the range of 0.1 to 10% by weight of the matrix. The matrix may be prepared using conventional polymer blending and mixing equipment.

FIG. 1 illustrates a simple bilayer transdermal drug delivery device, generally designated 10, which includes the matrix of the invention. Device 10 is composed of a drug-impermeable backing 11, and the invention matrix 12. Prior to use the device will include a basal release liner-layer (not shown) which is removed from the basal surface of the device to expose the matrix. The backing layer may be made from conventional transdermal device backing materials such as polyesters, aluminized polyesters, fluoroelastomers, elastomeric polyethylene, and siliconized or fluoro-coated polyesters. Device 10 may be made using conventional coating/laminating equipment. The invention matrix may be used in other transdermal drug delivery device embodiments such as, for instance, those having other backings and/or additional layers that alter the flux, flux profile, or mechanical properties of the device.

This invention is further illustrated by the following examples. These examples are not intended to limit the invention in any manner. Unless indicated otherwise, proportions are by weight.

EXAMPLE 1

Matrix for alprazolam (Xanax)

Mixtures of the hydrophobic drug alprazolam (5% by weight, the permeation enhancer propylene glycol monolaurate (PGML), and 75:25, 90:10 and 50:50 blends of a hydrophilic hydrogel adhesive (Rohm Plastoid L50) and hydrophobic silicone adhesive (Dow Corning HX 4201) were prepared by mixing the ingredients in a wide mouth glass bottle for 1 to 2 hr. at 25° C. The blends were cast into a polyester backing layer and dried at 70° C. for 60 minutes. The thickness of the layer of blend after drying was 10 mils.

For comparison, matrixes of 5% alprazolam, 5% PGML and either the hydrophobic or hydrophilic adhesive alone were prepared.

The flux of drug from these assemblies was determined by the procedure described in U.S. Pat. No. 5,069,909.

Figure 2:
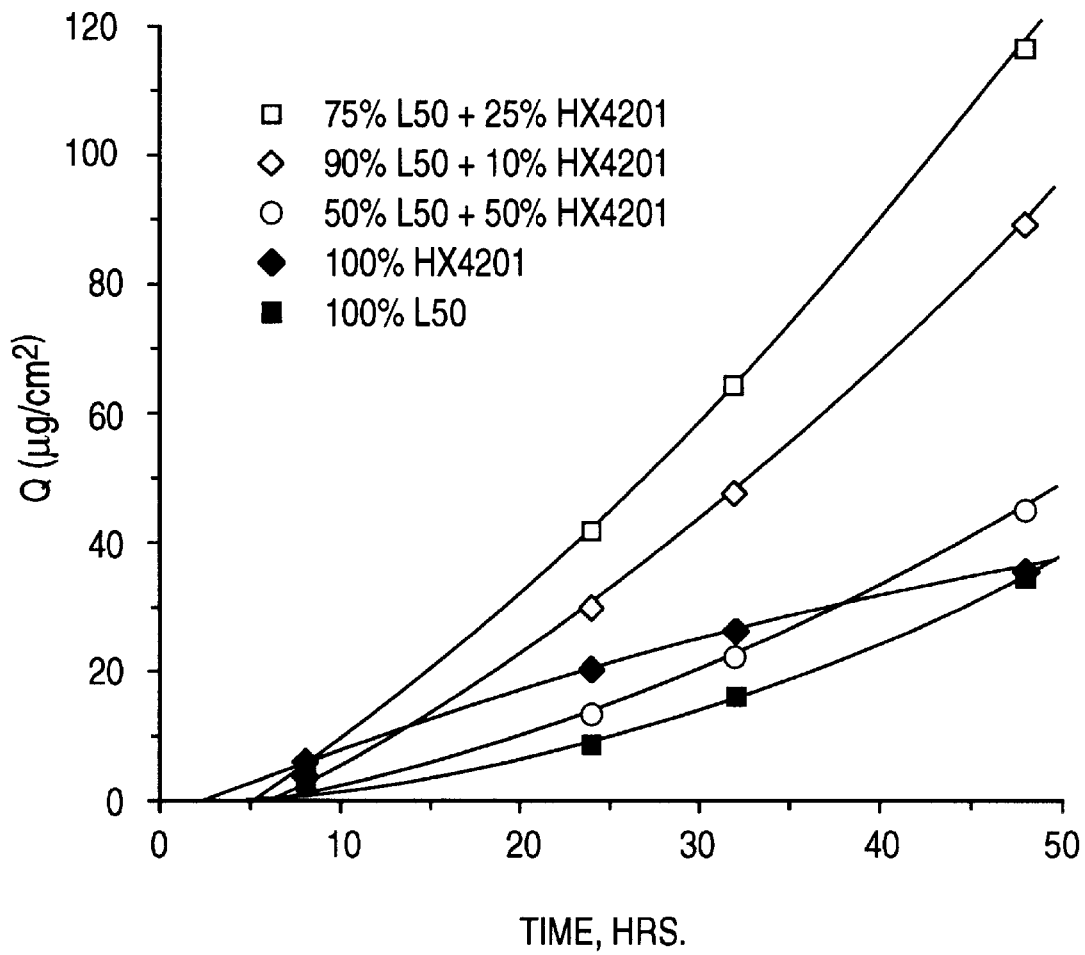
FIG. 2 is a graph showing the results of the flux tests of Example 1, infra.

The results of those studies are shown in FIG. 2. As indicated, the 75:25 and 90:10 matrixes exhibited substantially higher fluxes than the comparison matrixes. The 50:50 flux results indicate that for the particular drug and enhancer involved, a higher proportion of hydrophilic polymer is required to deliver higher drug fluxes.

EXAMPLE 2

Matrix for Nicardipine Hydrochloride

Mixtures of the hydrophilic drug nicardipine hydrochloride (5%), PGML (5%) and 90:10, 80:20, 75:25 and 50:50 blends of the hydrophilic and the hydrophobic adhesives described in Example 1 were made, cast onto backings, and tested as in Example 1.

Comparison matrixes containing only the hydrophobic or hydrophilic adhesive were also prepared and tested as in Example 1.

Figure 3:
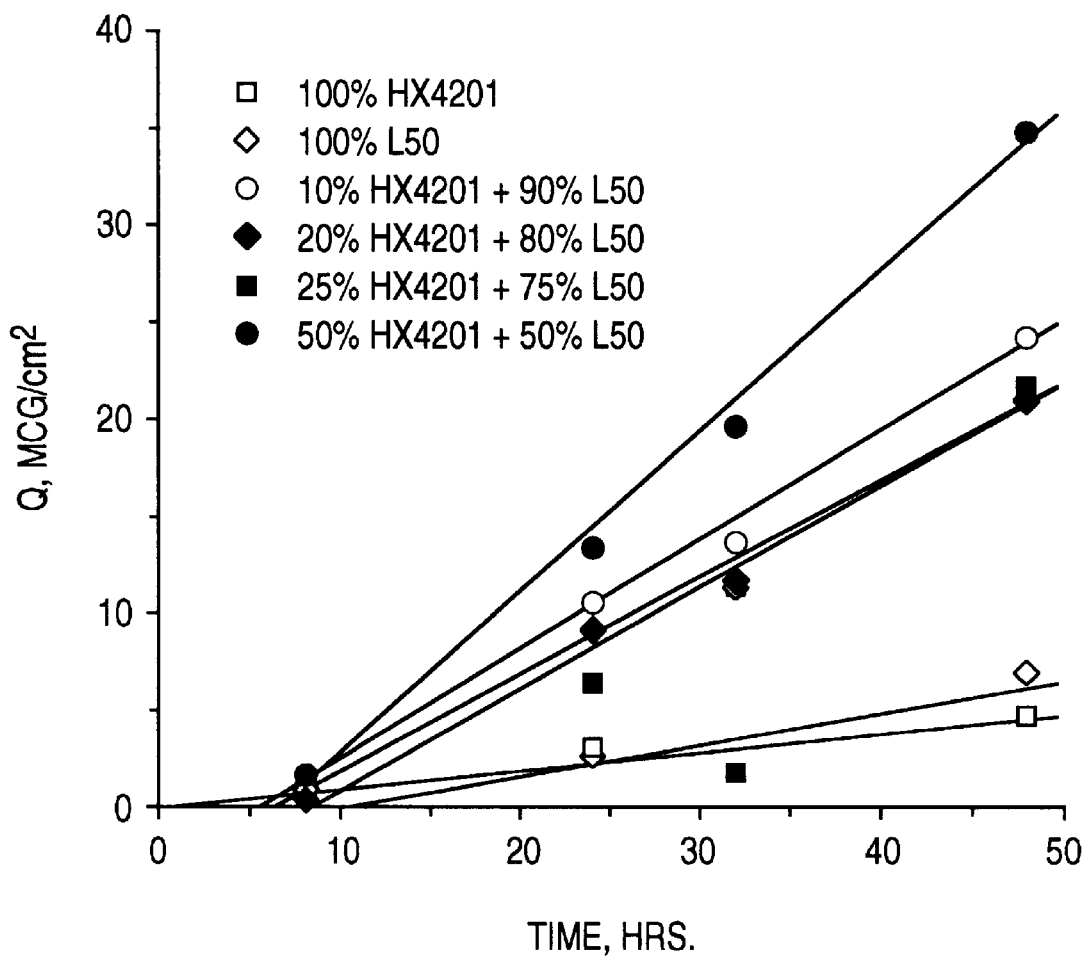
FIG. 3 is a graph showing the results of the flux tests of Example 2, infra.

The results of these studies are shown in FIG. 3. As depicted, the fluxes exhibited by the matrixes of the hydrophilic/hydrophobic adhesive blends were substantially higher than the fluxes exhibited by the matrixes of the single adhesives.

EXAMPLE 3

Mixtures of alprazolam (5%), PGML (5%), a 75:25 blend of the hydrophilic and hydrophobic polymers of Example 1, and 5% of an additional permeation enhancer (glycerol monoleate (GMO), methyl laurate (ML), or oleic acid (OA)) were prepared, cast onto a backing, and tested as in Example 1.

Comparison formulations in which the hydrophobic adhesive alone or the hydrophilic adhesive alone was substituted for the blend were also made and tested. The table below gives the results of those tests.

| Formulation | Flux (µg/cm/hr) |
| --- | --- |
| Comparisons | |
| GMO/L50 alone | 1.02 ± 0.40 |
| OA/L50 alone | 1.53 ± 0.47 |
| GMO/HX4201 alone | 1.05 ± 0.23 |
| ML/HX4201 alone | 0.95 ± 0.12 |
| OA/HX4201 alone | 2.12 ± 0.51 |
| Blends | |
| GMO/75:25 blend | 3.23 ± 0.84 |
| ML/75:25 blend | 2.74 ± 0.70 |
| OA/75:25 blend | 5.54 ± 0.83 |

As reported, the flux from the matrixes employing hydrophilic-hydrophobic polymer blends were substantially higher than the fluxes from the matrixes employing only the hydrophilic polymer or the hydrophobic polymer.

Modifications of the above-described modes for carrying out the invention that are obvious to those of skill in the fields of pharmaceutical formulation, transdermal drug delivery, pressure sensitive adhesives and related fields are intended to be within the scope of the following claims.

What is claimed is:

1. An adhesive transdermal drug delivery matrix comprising a homogeneous physical blend of:

(a) a drug that is capable of transdermal administration;

(b) a non-acrylate water-soluble hydrophilic polymer adhesive that is permeable to the drug, said hydrophilic polymer adhesive being selected from the group consisting of cellulose derivatives, polyvinyl alcohols, and polyacrylamides; and (c) a hydrophobic polymer adhesive that is permeable to the drug and substantially immiscible with the hydrophilic polymer adhesive, said hydrophobic polymer adhesive being selected from the group consisting of polysiloxanes, polyisobutylene, polyethylene, polystyrene-butadiene copolymers, polyurethanes, and polyether block amide copolymers;

wherein the hydrophilic polymer adhesive constitutes about 1% to 90% by weight of the total of the hydrophilic and hydrophobic polymer adhesives, the hydrophobic polymer adhesive constitutes about 10% to 99% by weight of the total of the hydrophilic and hydrophobic polymer adhesives, and the flux of drug from the blend is at least 30% greater than the flux of drug from either (b) or (c) alone.

2. The matrix of claim 1, further comprising a permeation enhancer.

3. The matrix of claim 1, wherein the drug is selected from the group consisting of alprazolam and nicardipine, and the hydrophobic polymer adhesive comprises a polysiloxane.

4. The matrix of claim 3, further comprising a permeation enhancer.

5. The matrix of claim 3, wherein the hydrophilic polymer adhesive constitutes 75% to 90% by weight of the total of the hydrophilic and hydrophobic polymers, and the hydrophobic polymer adhesive constitutes 10% to 25% by weight of the total of the hydrophilic and hydrophobic polymers.

6. The matrix of claim 4, wherein the permeation enhancer comprises propylene glycol monolaurate.

7. A transdermal drug delivery device comprising a laminated composite of:

(a) a backing layer; and (b) the matrix of claim 1.

8. An adhesive transdermal drug delivery matrix comprising a homogeneous physical blend of:

(a) a drug that is capable of transdermal administration;

(b) a water-soluble hydrophilic polymer adhesive that is permeable to the drug, said hydrophilic polymer adhesive being selected from the group consisting of methacrylic acid-copolymers, acrylate copolymers, cellulose derivatives, polyvinyl alcohols, and polyacrylamides; and (c) a non-siloxane hydrophobic polymer adhesive that is permeable to the drug and substantially immiscible with the hydrophilic polymer adhesive, said non-siloxane hydrophobic polymer adhesive being selected from the group consisting of polyisobutylene, polyethylene, polystyrene-butadiene copolymers, polyurethanes, and polyether block amide copolymers;

wherein the hydrophilic polymer adhesive constitutes about 1% to 90% by weight of the total of the hydrophilic and hydrophobic polymer adhesives, the hydrophobic polymer adhesive constitutes about 10% to 99% by weight of the total of the hydrophilic and hydrophobic polymer adhesives, and the flux of drug from the blend is at least 30% greater than the flux of drug from either (b) or (c) alone.

9. The matrix of claim 8, further comprising a permeation enhancer.

10. The matrix of claim 9, wherein the permeation enhancer comprises propylene glycol monolaurate.

11. The matrix of claim 8, wherein the hydrophilic polymer adhesive constitutes 75% to 90% by weight of the total of the hydrophilic and hydrophobic polymers, and the hydrophobic polymer adhesive constitutes 10% to 25% by weight of the total of the hydrophilic and hydrophobic polymers.

12. A transdermal drug delivery device comprising a laminated composite of:
   (a) a backing layer; and
   (b) the matrix of claim 8.

13. An adhesive transdermal drug delivery matrix comprising a homogeneous physical blend of:
   (a) a drug that is capable of transdermal administration;
   (b) a non-acrylate water-soluble hydrophilic polymer adhesive that is permeable to the drug, said hydrophilic polymer adhesive being selected from the group consisting of cellulose derivatives, polyvinyl alcohols, and polyacrylamides; and
   (c) a non-siloxane hydrophobic polymer adhesive that is permeable to the drug and substantially immiscible with the hydrophilic polymer adhesive, said hydrophobic polymer adhesive being selected from the group consisting of polyisobutylene, polyethylene, polystyrene-butadiene copolymers, polyurethanes, and polyether block amide copolymers;

wherein the hydrophilic polymer adhesive constitutes about 1% to 90% by weight of the total of the hydrophilic and hydrophobic polymer adhesives, the hydrophobic polymer adhesive constitutes about 10% to 99% by weight of the total of the hydrophilic and hydrophobic polymer adhesives and the flux of drug from the blend is at least 30% greater than the flux of drug from either (b) or (c) alone.

14. The matrix of claim 13, further comprising a permeation enhancer.

15. The matrix of claim 14, wherein the permeation enhancer comprises propylene glycol monolaurate.

16. The matrix of claim 13, wherein the hydrophilic polymer adhesive constitutes 75% to 90% by weight of the total of the hydrophilic and hydrophobic polymers and the hydrophobic polymer adhesive constitutes 10% to 25% by weight of the total of the hydrophilic and hydrophobic polymers.

17. A transdermal drug delivery device comprising a laminated composite of:
   (a) a backing layer; and
   (b) the matrix of claim 13.

* * * * *